US007223985B2

(12) United States Patent
Rigler et al.

(10) Patent No.: US 7,223,985 B2
(45) Date of Patent: May 29, 2007

(54) SINGLE-CHANNEL MULTICOLORED CORRELATION ANALYSIS

(76) Inventors: Rudolf Rigler, 115, rue du Centre, 1015 St-Sulpice (CH); Per Thyberg, Luidnersgatan 10b, 11253 Stockholm (SE); Adrian Honegger, General-Guisan-Strasse 31, 4144 Arlesheim (CH)

( * ) Notice: Subject to any disclaimer, the term of this patent is extended or adjusted under 35 U.S.C. 154(b) by 179 days.

(21) Appl. No.: 10/488,005

(22) PCT Filed: Aug. 28, 2002

(86) PCT No.: PCT/EP02/09610

§ 371 (c)(1), (2), (4) Date: Feb. 27, 2004

(87) PCT Pub. No.: WO03/021240

PCT Pub. Date: Mar. 13, 2003

(65) Prior Publication Data
US 2004/0238756 A1 Dec. 2, 2004

(30) Foreign Application Priority Data
Aug. 28, 2001 (DE) ............................. 101 41 950
Mar. 12, 2002 (DE) ............................. 102 10 737

(51) Int. Cl.
*G01N 21/64* (2006.01)
(52) U.S. Cl. ............................................ 250/458.1
(58) Field of Classification Search ........ 250/458.1
See application file for complete search history.

(56) References Cited

U.S. PATENT DOCUMENTS 4,150,295 A    4/1979  Wieder
4,922,092 A *  5/1990  Rushbrooke et al. . 250/214 VT
5,294,799 A    3/1994  Aslund et al.
5,943,129 A *  8/1999  Hoyt et al. ................. 356/318
6,071,748 A *  6/2000  Modlin et al. ............. 436/174
6,252,664 B1*  6/2001  Barbera-Guillem ......... 356/417
6,444,476 B1*  9/2002  Morgan ..................... 436/172
6,563,585 B1*  5/2003  Rao et al. .................. 356/436

(Continued)

FOREIGN PATENT DOCUMENTS

EP          0 679 251 A     11/1995

(Continued)

OTHER PUBLICATIONS

Johansson M et al., "Design, fabrication, and Evaluation of a Multichannel Diffractive Optic Rotary Joint", Applied Optics, Optical Society of America, vol. 38, No. 8, Mar. 10, 1999, pp. 1302-1310.

(Continued)

*Primary Examiner*—Otilia Gabor
(74) *Attorney, Agent, or Firm*—Rothwell, Figg, Ernst & Manbeck, P.C.

(57) ABSTRACT

The invention relates to a method for determining luminescent molecules by means of optical excitation in confocal measurement volumes, different species of luminescent molecules in a sample being excited at respectively different times and the emission radiation originating from the different species from a measurement volume being captured by a single detector. Furthermore, an apparatus suitable for carrying out the method is disclosed.

36 Claims, 5 Drawing Sheets

U.S. PATENT DOCUMENTS 6,927,401 B1 * 8/2005 Palo .................. 250/458.1

FOREIGN PATENT DOCUMENTS

WO     WO 99 42884 A    8/1999
WO     WO 00 58715 A    10/2000
WO     WO 01 01112 A    1/2001

OTHER PUBLICATIONS

Schwille P et al., "Dual-Color Fluorescent Cross-Correlation Spectroscopy for Multicomponent Diffusional Analysis in Solution", Biophysical Journal, vol. 72, No. 4, Apr. 1997, pp. 1878-1886.

* cited by examiner

SINGLE-CHANNEL MULTICOLORED CORRELATION ANALYSIS

CROSS REFERENCE TO RELATED APPLICATION

This application is a 35 USC § 371 National Phase Entry Application from PCT/EP02/09610, filed Aug. 28, 2002, and designating the U.S.

DESCRIPTION

The invention relates to a method for determining luminescent molecules by means of optical excitation in confocal measurement volumes, different species of luminescent molecules in a sample being excited at respectively different times and the emission radiation originating from the different species from a measurement volume being captured by a single detector. Furthermore, an apparatus suitable for carrying out the method is disclosed.

The use of fluorescence correlation spectroscopy (FCS) for the detection of analytes is known. EP-B-0 679 251 discloses methods and apparatuses for the detection of analytes by means of fluorescence spectroscopy, the determination being carried out in a confocal measurement volume which is part of the sample to be examined.

Fluorescence correlation spectroscopy may be carried out in conjunction with a so-called cross-correlation analysis, two species of luminescent molecules in a confocal measurement volume, which species differ with regard to at least one optical property, being excited and the presence or the absence of a correlation between the two measurement signals being analyzed. One disadvantage of cross-correlation methods used hitherto is, however, that the emission radiations originating from the different luminescent species have had to be detected by separate detectors in each case.

One object on which the present application is based was to provide methods and apparatuses for determining luminescent molecules, in particular by means of multicolored fluorescence correlation spectroscopy, which permit a determination of cross-correlations in a simple manner.

Consequently, the invention relates to a method for determining luminescent molecules by means of optical excitation in confocal measurement volumes, comprising the steps of:

(a) providing a sample comprising luminescent molecules,
(b) irradiating the sample with an optical excitation and focusing device for optically exciting luminescent molecules in at least one confocal measurement volume which is part of the sample, and
(c) capturing and evaluating emission radiation from the at least one measurement volume, in a measurement volume, a plurality of species of luminescent molecules that differ with regard to an optical property being excited at respectively different times and the emission radiation originating from the different species being captured and evaluated by a single detector.

The method according to the invention constitutes a single-channel multicolored correlation analysis, it being possible for a plurality, e.g. 2, 3, 4 or even more, of species of luminescent molecules in a single measurement volume, which species differ with regard to at least one optical property, such as emission wavelength and/or luminescence decay time, to be excited and for the signals to be evaluated on a single detector.

For this purpose, preferably 2 or more, e.g. 3, separate light sources, in particular lasers having different wavelengths, e.g. $\lambda 1$, $\lambda 2$, $\lambda 3$, are used for the respective separate excitation of different species. Said separate light sources may be radiated or coupled into the confocal measurement volume at respectively different times by means of one or a plurality of adjustable optical switching elements and be used for exciting the emission therein. Examples of suitable adjustable optical switching elements are acousto-optical modulators, adjustable reflection elements, such as, for instance, piezocontrolled mirrors, adjustable diffraction elements, adjustable diffraction-optical elements and Kerr cells. In order to detect the signals, only a single detector is used per measurement volume, which detector alternately records the signals emitted by the different excited species and defines them by means of suitable measures, e.g. a digital coding signal. Furthermore, a signal processor, a data storage unit and a correlator are preferably connected to the detector.

The signal recorded by the detector is preferably evaluated with a coding signal in a correlator, said coding signal corresponding to the clock frequency of the different light sources. As an alternative, it is also possible to use energy-dispersive detectors which can distinguish between the individual types of emission radiation originating from the respectively different excited species. The clock frequency with which the different light sources are radiated onto the measurement volume is related to the measurement signal to be expected. Thus, when determining diffusion events where the diffusion time is e.g. in the region of about 1 ms, a clock frequency with a considerably shorter clock interval, e.g. with a clock interval of 0.1–10 µs (corresponding to 10–0.1 MHz), e.g. of about 1 µs (corresponding to 1 MHz), is set. The clock time is set correspondingly for other types of determinations.

From the time profile of the individual emission signals originating from respectively different luminescent species, e.g. $\mu 1$, $\mu 2$, $\mu 3$, it is possible to calculate autocorrelation functions (only taking an individual signal into account) and also cross-correlations (jointly taking a plurality of signals into account), e.g. $\mu 1 \times \mu 2$, $\mu 2 \times \mu 3$, $\mu 1 \times \mu 3$ or $\mu 1 \times \mu 2 \times \mu 3$. A multiplex method is thus involved, which, in principle, can be applied to a larger number of laser frequencies.

By means of corresponding electronic background analysis, it is possible to calculate a correlation and/or coincidence curve in the case of which it is possible to distinguish "correctly" occurring signals from those signals which arise as a result of undesirable interference (crosstalk) of a plurality of marking groups.

In order to improve the accuracy of the method, in particular in order to reduce a crosstalk of the emission lines $\mu 1$, $\mu 2$, $\mu 3$ and principally of the excitation lines $\lambda 1$, $\lambda 2$, $\lambda 3$, it is possible to use dichroic filters and/or blocking filters, e.g. interference filters of different orders or notch filters for regulating the radiation, e.g. for a selective transmissivity at specific wavelengths.

A particularly preferred embodiment of the method according to the invention comprises a parallel determination of luminescent molecules in a plurality of samples. In this case, the light radiated from the optical excitation device may be split into multiple light beams or foci which are focused onto measurement volumes in a plurality of samples. In a particularly preferred embodiment, the radiated light is split by using one or a plurality of diffractive optical elements, as described in DE 101 26 083.0. In a particularly preferred manner, a diffractive optical element which is arranged upstream of the beam combination in the beam path is used for each light source.

Diffractive optical elements that may be used are, by way of example, three-dimensional optical gratings which, if appropriate, are applied to an optically transparent carrier and diffract light passing through and it is possible to generate a predetermined diffraction pattern, i.e. a desired arrangement of multiple optical foci, in arbitrary arrangements in the object plane by means of constructive and destructive interference. In this case the multiple optical foci are expediently formed by 1st order interferences, only minor light losses occurring as a result of 0th- or higher-order interferences.

The production of suitable diffractive optical elements is described for example in the dissertation by F. Nikolaef at the Chalmers Institute of Technologies (1999), in the dissertation by M. Johansson at the Chalmers Institute of Technologies (2001) and in the publication Johansson and Hard (Applied Optics 38(1999), 1302–1310). Suitable materials for producing the optical elements are plastics, glass and composites or other materials having optical transparency for a given wavelength which can be processed by means of photolithographic etching.

A preferred embodiment of the method according to the invention relates to the detection of luminescent molecules in the confocal measurement volumes by means of fluorescence correlation spectroscopy. The method may be carried out in principle according to the method described in EP-B-0 679 251. In this case, the measurement of one or a few analyte molecules is preferably effected in a measurement volume, the concentration of the analyte molecules to be determined preferably being $\leq 10^{-6}$ mol/l and the measurement volume preferably being $\leq 10^{-14}$ l. Substance-specific parameters are determined, which are determined by means of luminescence measurement at the analyte molecules. These parameters may be translation diffusion coefficients, rotation diffusion coefficients and/or the excitation wavelength, the emission wavelength and/or the lifetime of an excited state of a luminescent molecule or the combination of one or more of these measurement quantities. For specifics about equipment details, reference is made to the disclosure of EP 0 679 251.

A preferred feature of the method according to the invention is that the distance between the measurement volume in the sample liquid and the focusing optical arrangement of the light source is $\geq 1$ mm, preferably 1.5 to 10 mm and particularly preferably 2 to 5 mm. It is furthermore preferred for a gas phase region, which may contain air, protective gas or vacuum, to be arranged between the carrier containing the sample liquid and the optical focusing device. Methods and apparatuses for carrying out FCS with a large distance between focusing optical arrangement and confocal measurement volume are described in DE 101 11 420.6. For certain applications, however, it is also possible, of course, to choose a smaller distance between focusing optical arrangement and measurement volume of <1 mm. Equally, there may also be a direct contact between sample and focusing optical arrangement, e.g. through the use of an immersion liquid.

The method according to the invention is suitable in principle for carrying out any desired determination methods. A preferred embodiment relates to the determination of an analyte in a sample, e.g. for diagnostic applications or for screening for the purpose of identifying active substances which interact with a target substance. For this purpose, one or more analyte-binding substances which carry a marking group, in particular fluorescence marking group, that can be detected by luminescence measurement are added to the sample. In this case, the method according to the invention preferably comprises a determination of the binding of the marking substance to the analytes to be detected. This detection may be effected for example by means of multi-colored cross-correlation determination using at least two different markings, in particular fluorescence markings, whose correlated signal within the measurement volume is determined. This cross-correlation determination is described for example in Schwille et al. (Biophys. J. 72 (1997), 1878–1886) and Rigler et al. (J. Biotechnol. 63 (1998), 97–109).

The method according to the invention is suitable in particular for the detection of biomolecules e.g. nucleic acids, proteins or other analyte molecules which occur in living organisms, in particular in mammals such as humans. Furthermore, it is also possible to detect analytes which have been produced from biological samples in vitro, e.g. cDNA molecules which have been produced from mRNA by reverse transcription, or proteins which have been produced from mRNA or DNA by in vitro translation. The method is furthermore suitable for the detection of analytes which are present as elements of a library and are intended to exhibit predetermined characteristics, e.g. binding to the detection reagent. Examples of such libraries are phage libraries or ribosomale libraries.

In a particularly preferred embodiment, the determination comprises a nucleic acid hybridization, one or more luminescence-marked probes binding to a target nucleic acid as analytes. Such hybridization methods may be used for example for the analysis of gene expression, e.g. in order to determine a gene expression profile, or for the analysis of mutations, e.g. single-nucleotide polymorphisms (SNP). The method according to the invention is also suitable, however, for determining enzymatic reactions and/or for determining nucleic acid amplifications, in particular in a thermocycling process. Preferred methods for determining nucleic acid polymorphisms are described in DE 100 56 226.4 and DE 100 65 631.5. A two-colored or multicolored cross-correlation determination is particularly preferably carried out in this case.

In a further particularly preferred embodiment, the determination comprises the detection of a protein-protein or protein-ligand interaction, in which case e.g. low-molecular-weight active substances, peptides, nucleic acids, etc. may be used as protein ligands. A two-colored or multicolored correlation measurement is preferably carried out for such determinations as well.

In an alternative preferred embodiment, so-called "molecular beacon" probes or primers may be used, which—if they are present in the free form—give rise to a different measurement signal in respect of the luminescence intensity and/or decay time than in the bound state.

A further preferred embodiment of the invention comprises a method for the selection of particles in a substance library, a particle having a predetermined property being selected from a population, comprising a multiplicity of different particles. For this purpose, preferably, a population of different particles is provided, particles having a predetermined property are marked, the particles are conducted in a microchannel through a detection element, comprising multiple confocal volume elements, in order to distinguish between marked and unmarked particles and marked particles are removed. The steps of conduction and removal are preferably repeated at least once, the concentration of the particles being reduced preferably by at least the factor $10^4$ in a subsequent cycle compared with a preceding cycle. The particles may be selected for example from cells, parts of cell surfaces, cell organelles, viruses, nucleic acids, proteins and low-molecular-weight substances. The method is also suitable for the selection of particles from a combinatorial library which may contain genetic packages such as phages, cells, spores or ribosomes. The particle population preferably contains more than $10^6$ and particularly preferably more than $10^{10}$ different particles. The particles are preferably marked with a luminescence marking group.

Yet another embodiment comprises carrying out a sequence analysis of polymers, in particular biopolymers, luminescent fragments of an analyte present in the sample being determined. This embodiment is suitable in particular for carrying out a nucleic acid sequencing. For this purpose, a carrier particle with a nucleic acid molecule immobilized thereon is preferably provided, essentially all the nucleotide components of at least one base type in at least one strand of the nucleic acid molecule bearing a fluorescence marking. The carrier particle is introduced into a sequencing apparatus comprising a microchannel and retained there, e.g. by means of an IR capture laser, and individual nucleotide components are progressively cleaved from the immobilized nucleic acid molecule, e.g. by treatment with an exonuclease. The cleaved nucleotide components are then conducted through a microchannel, preferably by means of a hydrodynamic flow, and the base sequence of the nucleic acid molecule is determined there in confocal volume elements on the basis of the sequence of the cleaved nucleotide components.

In a preferred embodiment, light beams originating from the light sources are split into a plurality of optical foci. The light beam is preferably split into 2–32, in particular into 4–16, optical foci. By using a suitable focusing optical arrangement, confocal volume elements are imaged in the sample from said optical foci. The confocal volume elements expediently have a size of $10^{-18}$ to $10^{-9}$ l, preferably of $10^{-18}$ to $10^{-12}$ l and particularly preferably of $10^{-16}$ to $10^{-14}$ l.

In order to capture radiation, in particular emission radiation from the multiple confocal volume elements, use is preferably made in each case of a separate detector per volume unit or a spatially resolving detection matrix, e.g. an avalanche photodiode matrix or an electronic detector matrix, e.g. a CCD camera.

Splitting the light beam into a plurality of optical foci permits parallel determination in separate confocal volume elements. In a preferred embodiment, these confocal volume elements are provided in respective separate containers of a carrier, preferably of a microstructure.

The volume of these containers is preferably in the range of $\leq 10^{-6}$ l and particularly preferably $\leq 10^{-8}$ l to $10^{-12}$ l. Thus, the carrier may comprise a microwell structure with a plurality of depressions for receiving sample liquid, which for example have a diameter of between 10 and 1000 µm. Suitable microstructures are described e.g. in DE 100 23 421.6 and DE 100 65 632.3. These microstructures may be used for example for determining a nucleic acid hybridization in solution. The carrier furthermore preferably comprises at least one temperature control element, e.g. a Peltier element, which enables temperature regulation of the carrier and/or individual sample containers therein.

The carrier used for the method is expediently configured in such a way that it enables optical detection of the sample. A carrier which is optically transparent at least in the region of the sample containers is therefore preferably used. The carrier may in this case either be fully optically transparent or contain an optically transparent base and an optically opaque covering layer with cutouts in the sample containers. Suitable materials for carriers are, for example, composite carriers made of metal (e.g. silicon for the covering layer) and glass (for the base). Carriers of this type may be produced for example by applying a metal layer with predetermined cutouts for the sample containers onto the glass. Plastic carriers, e.g. made of polystyrene or polymers based on acrylate or methacrylate, may alternatively be used. It is furthermore preferred for the carrier to have a cover for the sample containers, in order to provide a system which is closed and essentially isolated from the surroundings during the measurement.

In a particularly preferred embodiment, a carrier is used which contains a lens element arranged in the beam path between measurement volume and light source or detector of the optical apparatus. By way of example, the lens element may be fitted at the bottom of a microwell structure. A lens element of this type may, for example, be produced by heating and shaping a photoresist using a master mold, e.g. made of metal such as silicon, and then applied onto the carrier. As an alternative—e.g. when using carriers made of a fully plastic structure—the lens elements may be integrated into the carrier, e.g. produced during production by injection molding. The numerical aperture of the optical measuring arrangement may be increased by using a lens element, preferably a convex lens element. This numerical aperture is preferably in the range of 0.5 to 1.2.

The carrier is furthermore preferably coated with a transparent antireflection coating in order to produce a higher refractive index. By way of example, transparent oxides or nitrides may be used as antireflection coatings. Antireflection coatings are preferably also used on the optical arrangement.

Furthermore, electric fields may be generated in the carrier, in particular in the region of the sample containers, in order to achieve a concentration of the analytes to be determined in the measurement volume. Examples of electrodes which are suitable for generating such electric fields are described e.g. in DE 101 03 304.4.

The molecule to be determined may be bound to a carrier particle—in particular in the case of a determination in the microwell format or in the case of single molecule sequencing. The carrier particle has a size which enables movement in microchannels and retention at a desired position within a sequencing apparatus. The particle size is preferably in the range of 0.5–10 µm and particularly preferably 1–3 µm. Examples of suitable materials of carrier particles are plastics such as polystyrene, glass, quartz, metals or semimetals such as silicon, metal oxides such as silicon dioxide or composite materials which contain a plurality of the above-mentioned components. Particular preference is given to using optically transparent carrier particles, for example made of plastics, or particles having a plastic core and a silicon dioxide shell.

Nucleic acid molecules are preferably immobilized on the carrier particle via their 5' end, e.g. by means of covalent or noncovalent interaction. Polynucleotides are particularly preferably bound to the carrier by high-affinity interactions between the partners of a specific binding pair, e.g. biotin/ streptavidin or avidin, etc. As an alternative, nucleic acid molecules may also be bound to the carrier by means of adsorption or covalently.

Carrier particles to which only a single nucleic acid molecule is bound are preferably used. Carrier particles of this type may be produced by the nucleic acid molecules provided for the determination being brought into contact with the carrier particles in a molar ratio of preferably 1:5 to 1:20, e.g. 1:10, under conditions under which the nucleic acid molecules are immobilized on the carrier.

The carrier-bound nucleic acid molecules, e.g. DNA molecules or RNA molecules, may be present in single-stranded form or double-stranded form. The nucleic acid molecules are preferably present in single-stranded form. When used for sequencing, essentially all the nucleotide components, e.g. at least 90%, preferably at least 95%, of all the nucleotide components, of at least one base type carry a fluorescence marking group. It is also possible for essentially all the nucleotide components of at least 2 base types, for example 2, 3 or 4 base types, to carry a fluorescence marking, each base type expediently containing a different fluorescence marking group. Nucleic acids marked in this way may be produced by enzymatic primer extension on a nucleic acid matrix using a suitable polymerase, e.g. a thermostable DNA polymerase. A precise description of this method is found in DE 100 31 840.1 and DE 100 65 626.9 and also the literature citations specified therein.

The present invention relates still further to an apparatus for determining luminescent molecules, in particular for carrying out a method as described above, comprising (a) a carrier for receiving a sample which contains a plurality of different species of luminescent molecules, (b) an optical excitation and focusing device, comprising a plurality of separate light sources, and an adjustable optical switching element for coupling the separate light sources at different times onto a confocal measurement volume which is part of the sample, and (c) an optical detection device, comprising in each case a single detector per measurement volume for detecting luminescence.

The carrier is preferably a microstructure with a plurality of containers, preferably at least 10, particularly preferably at least $10^2$ containers, for receiving a sample liquid, in which case the separate containers may originate from one or more sources. The introduction of the sample liquid into the containers of the carrier may be effected e.g. by means of a piezoelectric liquid delivery apparatus.

The containers of the carrier are configured in such a way that they enable binding of the detection reagent to the analyte in solution. The containers are preferably depressions in the carrier surface, in which case said depressions may in principle have any desired form, for example circular, square, rhomboid, etc. The carrier may even comprise $10^3$ or more separate containers.

As an alternative, the carrier may also contain a microchannel structure with one or more microchannels which are suitable in particular for a single-molecule sequencing method as described in DE 100 31 840.1 and DE 100 65 626.9 or for a particle selection method as described in DE 100 31 028.1.

The optical excitation and focusing device comprises a plurality of strongly focused light sources, preferably laser beams, which are focused onto the measurement volume in the sample liquid by means of corresponding optical devices. The individual laser beams are focused onto the measurement volume by means of adjustable optical switching elements at respectively different times in a predetermined clock timing.

Furthermore, the optical device preferably contains dichroic filters and/or blocking filters and also—for splitting the laser beams into multiple foci—one or a plurality of diffractive optical elements. The diffractive optical elements may be arranged upstream and/or downstream of the combination of the different laser beams. Preferably, a respective diffractive optical element is used for each laser upstream of the beam combination.

The detection device may contain for example a fiber-coupled avalanche photodiode detector or an electronic detector. However, it is also possible to use excitation and/or detection matrices comprising a point matrix of laser points produced by a diffraction optical arrangement or a quantum well laser, as well as a detector matrix produced by an avalanche photodiode matrix or an electronic detector matrix, e.g. a CCD camera.

The carrier may be provided in prefabricated form, a plurality of separate containers of the carrier being filled with luminescence-marked detection reagents, preferably luminescence-marked hybridization probes or primers. The carrier containing the detection reagents is then expediently dried.

In a preferred embodiment of the invention, a prefabricated carrier is provided which contains a multiplicity of separate containers, e.g. 100 containers, which are respectively filled with different detection reagents, e.g. reagents for the detection of a nucleic acid hybridization such as primers and/or probes. This carrier may then be filled with a sample originating from an organism to be examined, e.g. a human patient, so that different analytes from a single sample are determined in the respective containers. Carriers of this type may be used for example to compile a gene expression profile, e.g. for the diagnosis of diseases, or for the determination of nucleic acid polymorphisms, e.g. for the detection of a specific genetic predisposition.

The invention will furthermore be explained by means of the accompanying figures.

FIG. 1 shows the diagrammatic illustration of an embodiment of the method according to the invention. Three light sources, e.g. lasers (1, 2, 3) having wavelengths λ1, λ2, and λ3, are connected by means of suitable optical switching elements, e.g. acousto-optical modulators, in order to enable the individual laser beams to be coupled into the beam path by means of a predetermined clock timing. The laser beam, which alternates between the wavelengths λ1, λ2 and λ3 in the predetermined clock timing impinges on a dichroic filter (6), which directs said laser beam via a focusing objective (8) onto a confocal measurement volume in the sample (10). Emission radiation emerging from luminescent molecules in the sample (10) is conducted through the dichroic filter (6) and a blocking filter (12) and subsequently via a aperture (14) into a detector (16) with signal processor, data storage and correlator.

FIG. 2 shows a diagrammatic illustration of the time-dependent signal flow l(t) at the detector. The signal originating from the emission radiation μ1, μ2, μ3 from luminescent molecules situated in the sample is recorded by the detector and provided with a coding signal for the respective clock timing of the wavelengths λ1, λ2 and λ3. From the time profiles of μ1, μ2 and μ3, it is possible to calculate the corresponding autocorrelation and cross-correlation functions.

Figure 1:
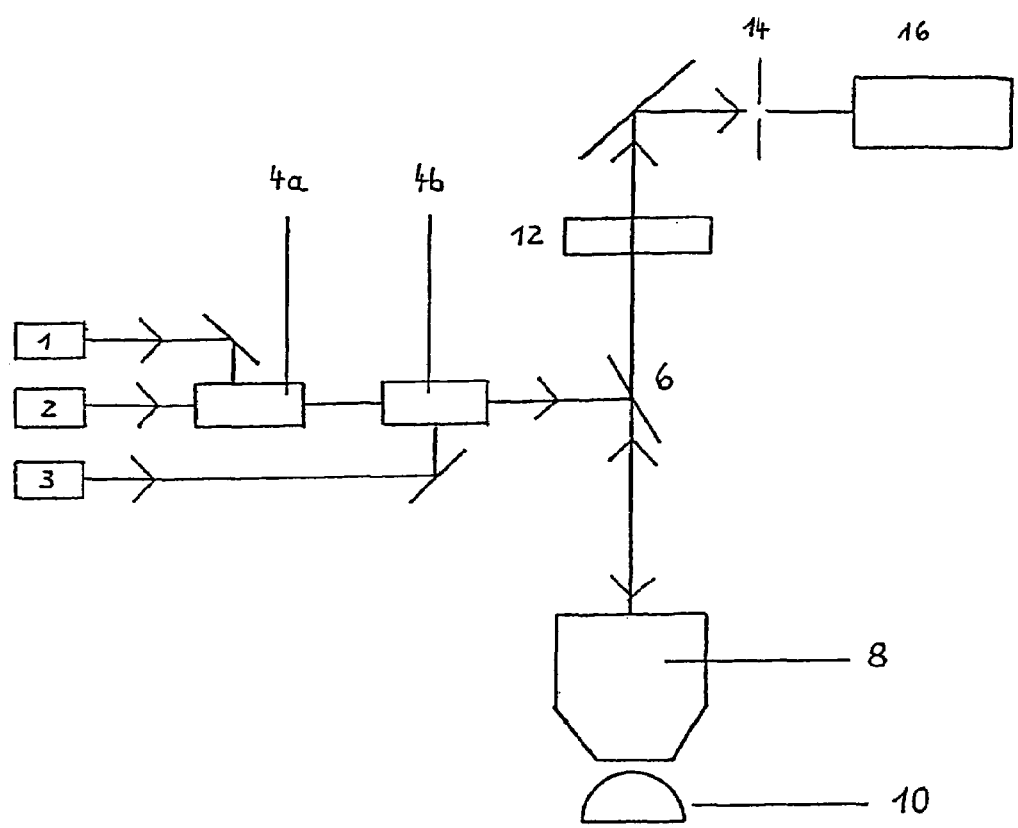
Figure 2:
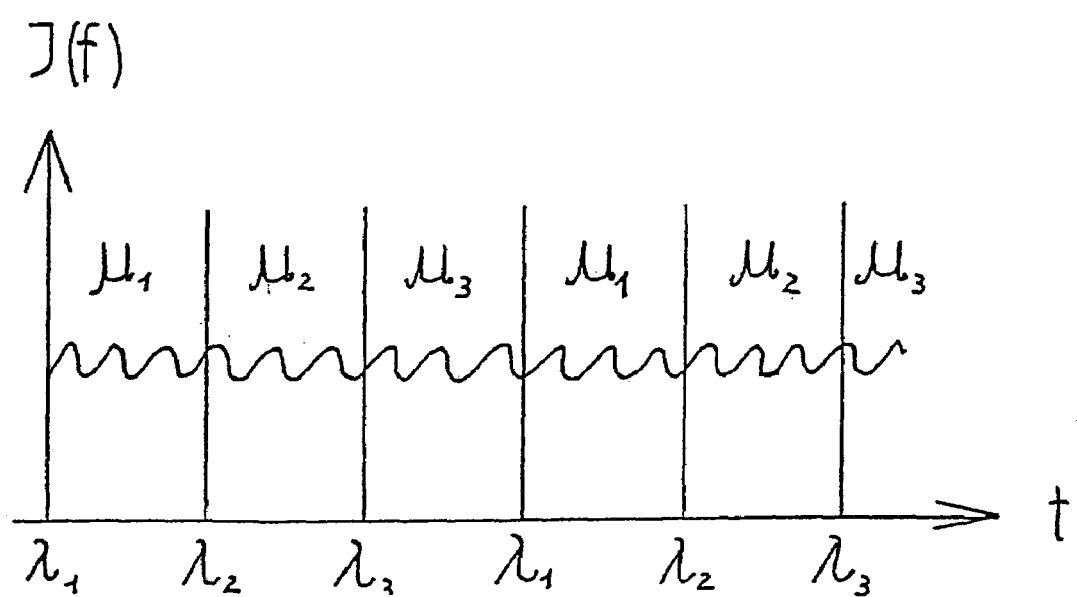
Figure 3:
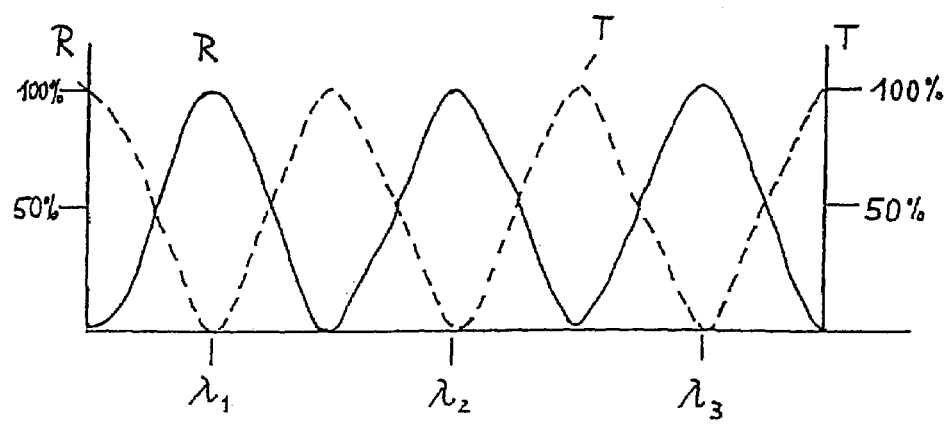
FIG. 3A shows the wavelength λ dependent reflection (R) and transmission (T) of the dichroic filter (6) in accordance with FIG. 1. The transmission is minimal at the excitation wavelengths λ1, λ2 and λ3.
FIG. 3B shows the wavelength dependent transmission (T) of a blocking filter (12) in accordance with FIG. 1. The transmission is minimal in the region of the excitation wavelengths λ1, λ2 and λ3, but is maximal in the region of the emission wavelengths μ1, μ2 and μ3 (not shown).
Figure 3:
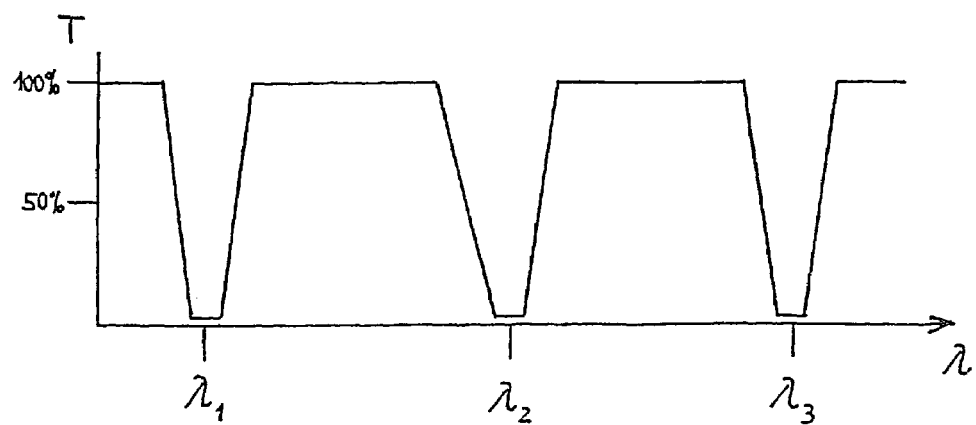
Figure 4:
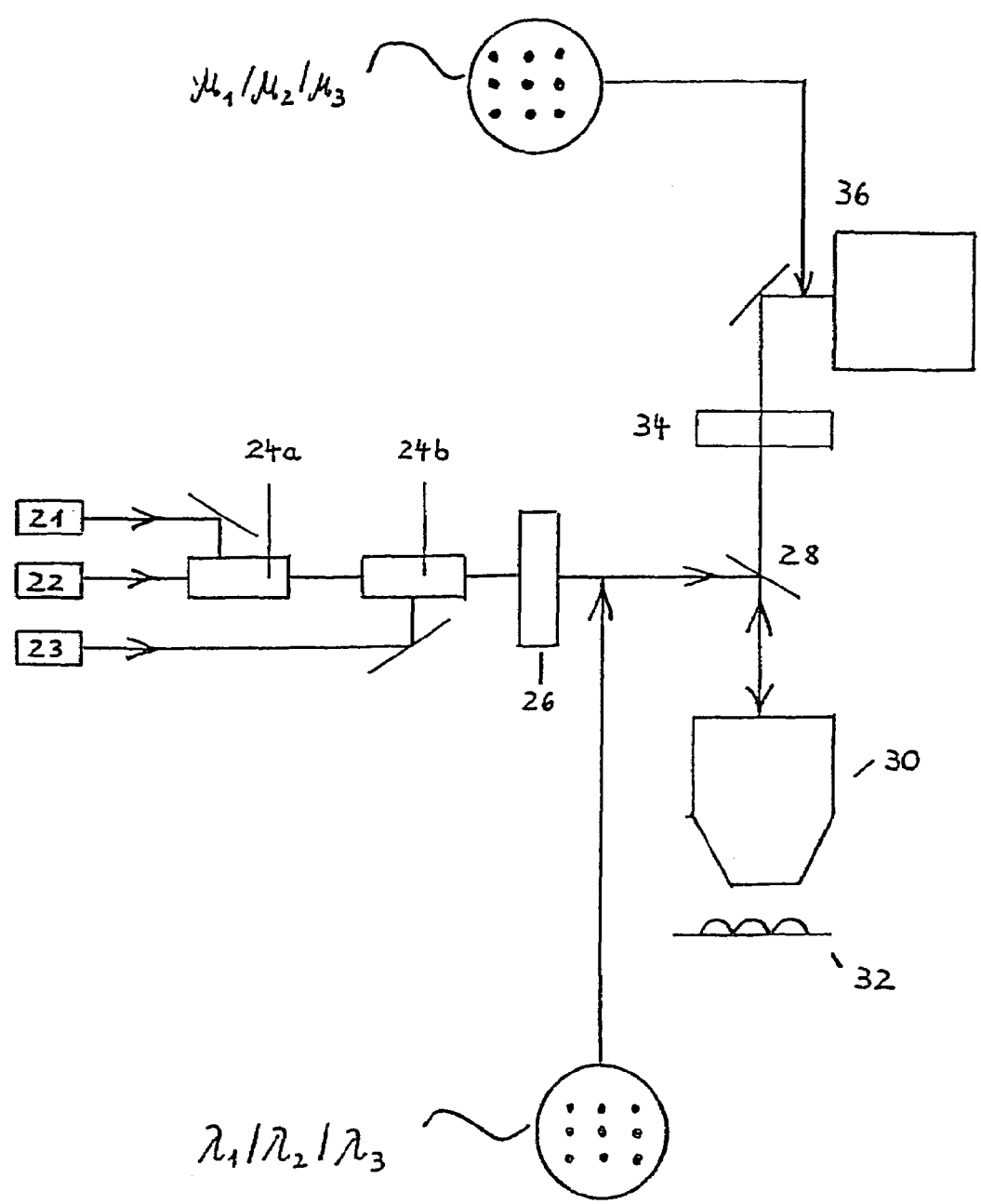

FIG. 4 shows the diagrammatic illustration of a particularly preferred embodiment of the method according to the invention. 3 lasers (21, 22, 23) are coupled into the beam path in a predetermined clock timing by means of optical switching elements (24a, 24b). The laser beam passes through a diffractive optical element (26) where it is is split into a multiplicity of optical foci, e.g. 9 optical foci (shown in cross section), with a wavelength $\lambda 1$, $\lambda 2$ and $\lambda 3$ that changes in the clock timing. The split light beam is conducted onto a sample matrix (12) via a dichroic mirror (28) and a focusing objective (10) comprising, if appropriate, a plurality of subelements. Said sample matrix comprises e.g. a plurality of separate samples each containing a measurement volume, in a manner corresponding to the matrix of the multiple optical foci. Emission radiation originating from the measurement volumes of the sample matrix (32) is directed through the dichroic filter (28) and a blocking filter (34) onto a detector matrix (36). The matrix of emission beams having a wavelength $\mu 1$, $\mu 2$, $\mu 3$—depending on the clock timing and the molecules excited in the sample—is shown in cross section. In the detector matrix (36), the signals originating from the individual measurement volumes are captured and evaluated in separate detectors.

Figure 5:
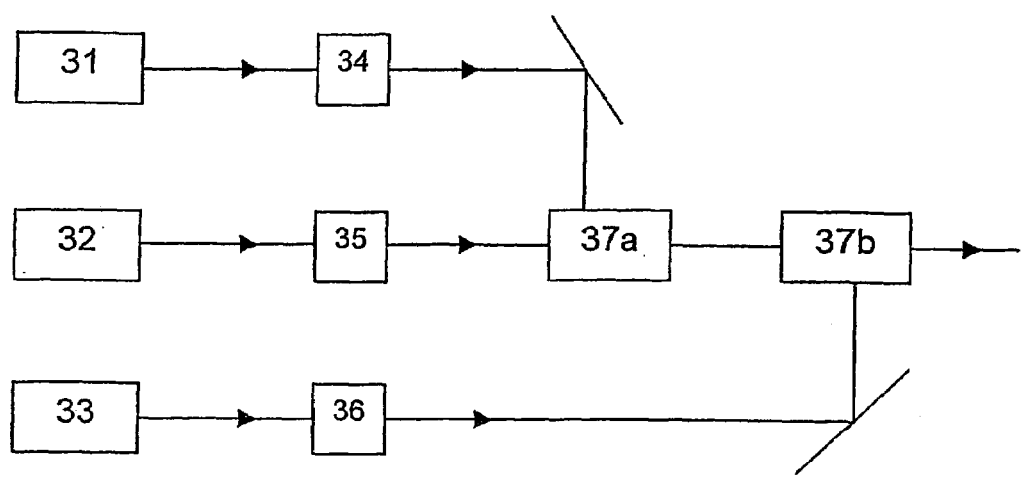

FIG. 5 shows a further particularly preferred embodiment. In this case, in a departure from the arrangement shown in FIG. 4, a diffractive optical element (34, 35, 36) is in each case arranged directly downstream of each laser (31, 32, 33). Consequently, each laser beam can be split into multiple optical foci before the beam combination is effected by means of optical switching elements (37a, 37b). Otherwise, the determination is carried out in accordance with FIG. 4.

The embodiments in accordance with FIGS. 4 and 5 are suitable for a single-channel multiplex multicolored correlation determination.

EXAMPLE

A fluorescence cross-correlation determination of 2 marking groups in a sample was carried out by means of two laser beams on the apparatus Confocor 2 (Zeiβ). The data were evaluated in such a way that a temporally alternating change in the wavelength of the excitation light was simulated. The alternating frequency was 1 MHz, i.e. the fluorescence originating from a first marking group was set to 0 for a time segment of 1 µs and the fluorescence originating from the second marking group was set to 0 for the next time segment of 1 µs. Consequently, the frequency for a complete cycle was 0.5 MHz (corresponding to a time duration of 2 µs).

200 million data points were recorded for a time duration of 1 s. Therefore, 20 data points were recorded per time segment of 1 µs. In order to simulate a delay which might arise as a result of a change in wavelength, 2 and 10 data points per time segment were additionally set to 0 (corresponding to a delay of 100 ns and 500 ns, respectively). The cross-correlation was calculated on the basis of the raw data of the apparatus.

It was found that the cross-correlation function can be evaluated despite a rapid repeated change in the wavelength of the excitation light. In particular in the case of a delay duration of $\geqq 200$ µs (corresponding to cross-correlation channels of 76 and higher), no significant differences from a standard evaluation were discernable.

The invention claimed is:

1. A method for determining luminescent molecules by means of optical excitation in confocal measurement volumes, comprising the steps of:

(a) providing a sample comprising a plurality of species of luminescent molecules that differ with regard to at least one optical property, (b) irradiating said sample with an optical excitation and focusing device for optically exciting said plurality of species of luminescent molecules at respectively different times in at least one confocal measurement volume, wherein the time lag between said different times is chosen to be shorter than the average duration of stay of a luminescent molecule in said confocal measurement volume, and (c) capturing and evaluating emission radiation originating from said plurality of species contained in said at least one confocal measurement volume by a single detector.

2. The method as claimed in claim 1, wherein 2, 3 or 4 species of luminescent molecules that differ with regard to the optical properties are excited.

3. The method as claimed in claim 1, wherein the optical excitation device comprises a plurality of separate light sources for respectively exciting different species in a measurement volume.

4. The method as claimed in claim 3, wherein the separate light sources are coupled into the beam path at respectively different times by means of an adjustable optical switching element.

5. The method as claimed in claim 4, wherein the adjustable optical switching element is selected from acousto-optical modulators, reflection elements, diffraction elements, diffractive optical elements and Kerr cells.

6. The method as claimed in claim 1, wherein a cross-correlation of at least 2 of the excited luminescent species is determined.

7. The method as claimed in claim 1, wherein the excited luminescent species differ in at least one optical property, selected from emission wavelength and luminescence decay time.

8. The method as claimed in claim 1, wherein the step of evaluating emission radiation from the at least one measurement volume comprises the setting of a clock signal on the detector.

9. The method as claimed in claim 8, wherein the frequency of the clock signal is set in the range of 10–0.1 MHz.

10. The method as claimed in claim 1, wherein the step of evaluating emission radiation from the at least one measurement volume comprises the use of an energy-dispersive detector.

11. The method as claimed in claim 1, wherein the excitation light radiated onto the measurement volume and the emission light radiated by the measurement volume are optically filtered.

12. The method as claimed in claim 11, wherein dichroic filters and blocking filters are used for the optical filtering.

13. The method as claimed in claim 11, wherein dichroic filters are used for the optical filtering.

14. The method as claimed in claim 11, wherein blocking filters are used for the optical filtering.

15. The method as claimed in claim 1, wherein an electronic background analysis is carried out in order to filter out signals which arise as a result of undesirable interference of a plurality of species of luminescent molecules.

16. The method as claimed in claim 1, wherein said at least one confocal measurement volume is contained in a carrier comprising a plurality of separate volume containers.

17. The method as claimed in claim 16, wherein the carrier comprises a microwell structure with a plurality of depressions which preferably have a diameter of between 10 and 1000 μm.

18. The method as claimed in claim 1, wherein a parallel determination of luminescent molecules in a plurality of measurement volumes is carried out.

19. The method as claimed in claim 18, wherein a detection matrix, comprising a plurality of detectors, is used for the parallel capture of emission radiation from a plurality of measurement volumes, one detector respectively being provided for one measurement volume.

20. The method as claimed in claim 1, wherein said optical excitation and focusing device further comprises one or a plurality of diffractive optical elements to split an irradiating source.

21. The method as claimed in claim 20, wherein a separate diffractive optical element is used for each light source.

22. The method as claimed in claim 20, wherein the diffractive optical element used is a three-dimensional optical grating which is applied to an optically transparent carrier, diffracts light passing through and generates a pre-determined diffraction pattern, comprising multiple optical foci.

23. The method as claimed in claim 20, wherein the diffractive optical element used is a three-dimensional optical grating which is not applied to an optically transparent carrier, diffracts light passing through and generates a pre-determined diffraction pattern, comprising multiple optical foci.

24. The method as claimed in claim 1, wherein the distance between the measurement volume and the focusing device is $\geq 1$ mm.

25. The method as claimed in claim 24, wherein the distance between the measurement volume and the focusing device is 1.5–10 mm.

26. The method as claimed in claim 1, wherein the sample is thermally insulated from the light source and from the focusing device.

27. The method as claimed in claim 1 for determining an analyte present in the sample.

28. The method as claimed in claim 27, wherein a nucleic acid analyte is determined.

29. The method as claimed in claim 27, wherein the determination comprises:
    (a) a mutation analysis for nucleic acids
    (b) a gene expression analysis
    (c) a nucleic acid sequencing or
    (d) a particle selection.

30. An apparatus for determining luminescent molecules, in particular for carrying out a method as claimed in claim 1, comprising
    (a) a carrier for receiving at least one sample which contains a plurality of different species of luminescent molecules,
    (b) an optical excitation and focusing device, comprising a plurality of separate light sources, an adjustable optical switching element for coupling the separate light sources at different times
    (c) at least one separate diffractive optical element per light source for splitting the light radiated from the optical excitations device into multiple foci, which can be focused onto respectively different confocal measurement volumes, and
    (d) an optical detection device, comprising in each case a single detector per measurement volume for detecting luminescence.

31. The apparatus as claimed in claim 30, wherein it furthermore contains one or a plurality of diffraction-optical elements for splitting the excitation light into multiple foci.

32. The apparatus as claimed in claim 30, wherein a separate diffractive optical element is provided for each light source.

33. The apparatus as claimed in claim 30, wherein it furthermore contains a detector matrix, comprising a plurality of detectors, for the parallel capture of emission radiation from a plurality of measurement volumes, one detector being provided for in each case one measurement volume.

34. The use of the apparatus as claimed in claim 30 for fluorescence correlation spectroscopy.

35. The method as claimed in claim 1, wherein the excitation light radiated onto the measurement volume is optically filtered.

36. The method as claimed in claim 1, wherein the emission light radiated by the measurement volume is optically filtered.

* * * * *